United States Patent [19]

Mennen

[11] 4,355,113
[45] Oct. 19, 1982

[54] OVER THE COUNTER SWAB KIT FOR SELF DETECTION OF GONORRHEA IN THE MALE USING SALINE AMPULE

[76] Inventor: Frederick C. Mennen, 506 Clay St., La Porte, Ind. 46350

[21] Appl. No.: 275,170

[22] Filed: Jun. 19, 1981

[51] Int. Cl.³ .......................................... G01N 33/50
[52] U.S. Cl. ................... 435/295; 23/230 B; 422/61; 422/102; 435/292; 435/296; 435/810; 435/871
[58] Field of Search ............... 422/61, 102; 23/230 B; 435/292, 295, 296, 871, 810

[56] References Cited

U.S. PATENT DOCUMENTS

| | | | |
|---|---|---|---|
| 3,446,596 | 5/1969 | Salivar et al. | 422/58 X |
| 3,954,563 | 5/1976 | Mennen | 435/295 |
| 3,954,564 | 5/1976 | Mennen | 435/295 |
| 4,272,479 | 6/1981 | Huneke et al. | 422/61 X |
| 4,300,910 | 11/1981 | Pannwitz | 422/61 X |

Primary Examiner—Ronald E. Serwin
Attorney, Agent, or Firm—Abraham A. Saffitz

[57] ABSTRACT

An over the counter swab kit for self detection of gonorrhea in the male using saline ampul. A method wherein a pledget in the form of fibrous material is impregnated with a compound which reacts with *Neisseria gonorrhea* to produce a color change. The pledget, before the test, is in a dry condition and is activated by a wetting agent such as saline, when placed in contact with the pledget. The chemical compound used and incorporated into the pledget is selected from a group consisting of phenylenediamines. A sufficient amount of saline is held within a frangible ampul to wet the pledget and then to be drawn by capillary action through the swab on which a sample of exudate as a specimen is placed. The chemical compound is in the form of a mineral acid salt which dissolves in the saline and is transported by capillary action through the pledget into the swab. A purple color is created on the tip of the swab at the site of the bacteria and is a positive test for gonorrhea. There is also disclosed a novel method for the manufacture of the novel swab kit for self detection of gonorrhea in the male.

5 Claims, 13 Drawing Figures

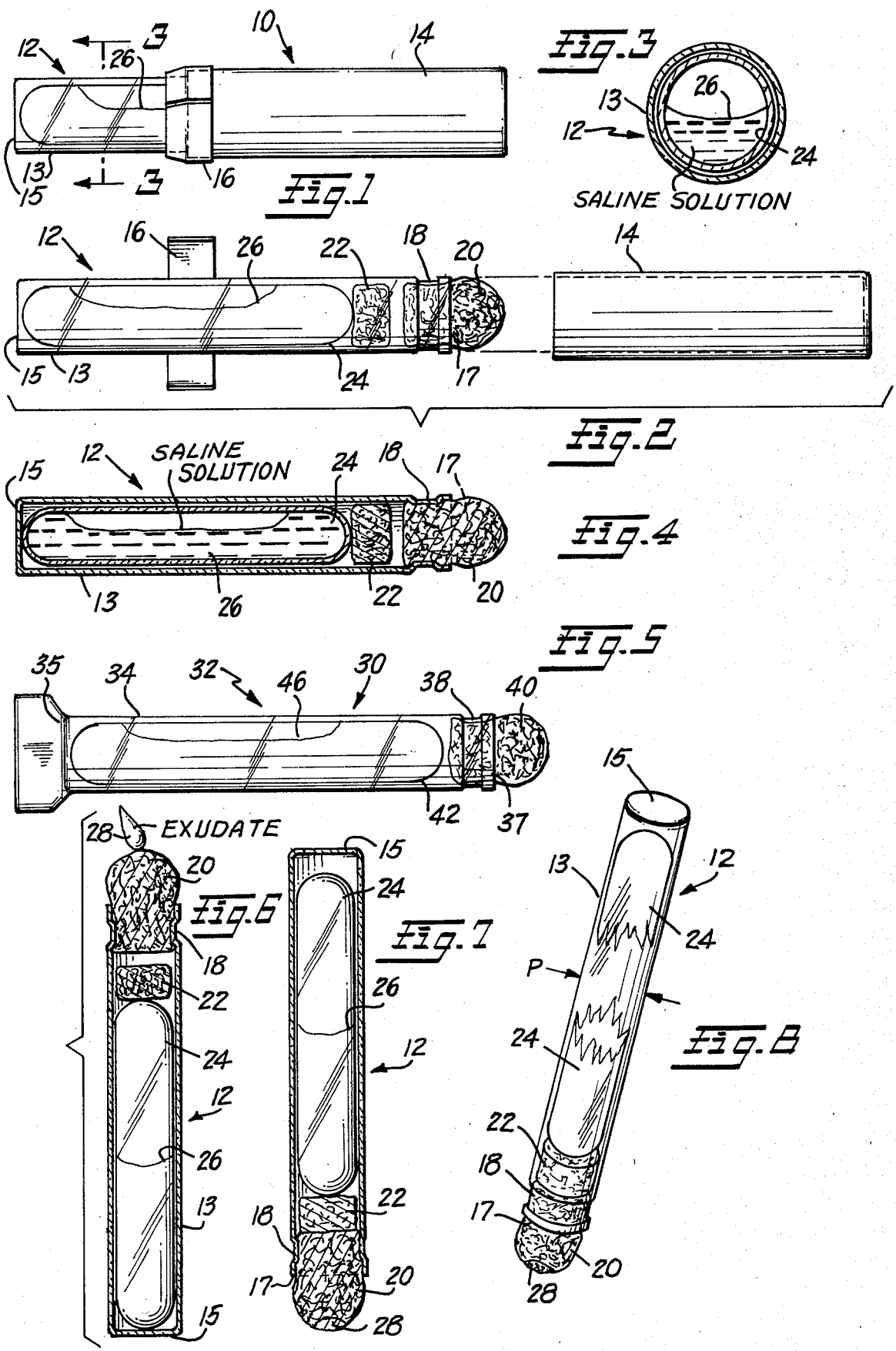

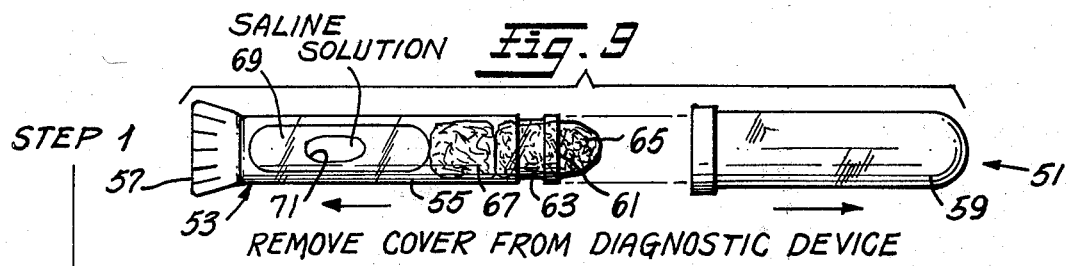
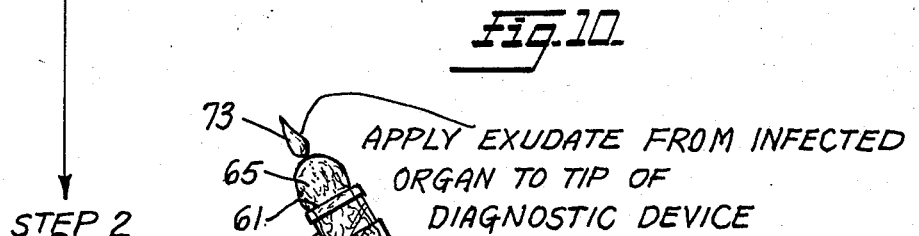
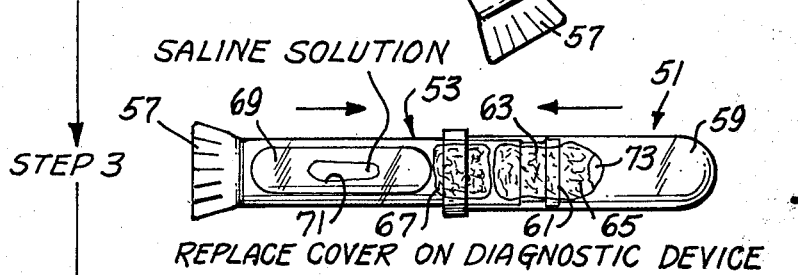
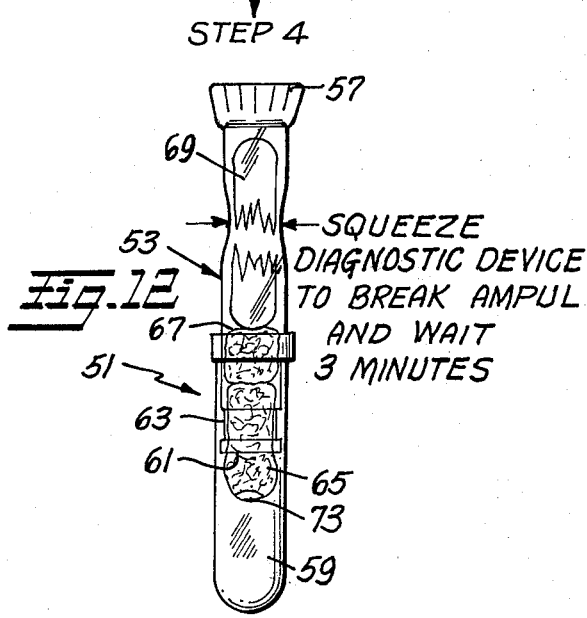
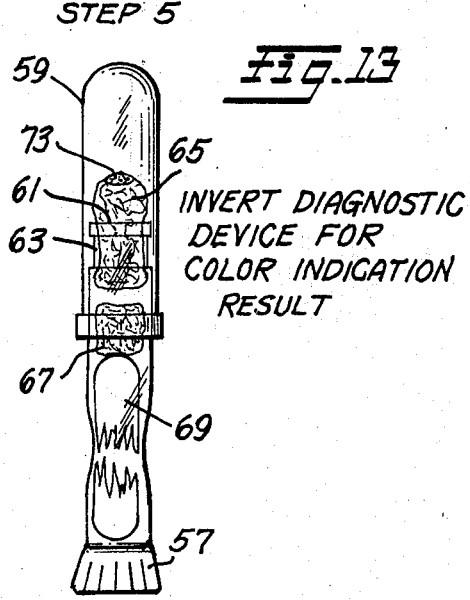

OVER THE COUNTER SWAB KIT FOR SELF DETECTION OF GONORRHEA IN THE MALE USING SALINE AMPULE

CROSS-REFERENCE TO RELATED APPLICATIONS

Frederick C. Mennen, application filed Oct. 29, 1971, entitled Method and Instrument for the Detection of *Neisseria Gonorrheae* Without Culture, now U.S. Pat. No. 3,876,503 granted Apr. 8, 1975.

Frederick C. Mennen, application filed Dec. 30, 1974, entitled Instrument for the Detection of *Neisseria Gonorrhoeae*, Ser. No. 537,593, allowed Oct. 20, 1976, final fee paid Jan. 21, 1977, now U.S. Pat. No. 4,018,653 granted Apr. 19, 1977.

Frederick C. Mennen, application filed Mar. 28, 1975, entitled Apparatus Especially Useful for Detection of *Neisseria Gonorrhoeae* and the Like in Females, Ser. No. 563,300, granted May 4, 1976 now U.S. Pat. No. 3,954,563.

Frederick C. Mennen, application filed Mar. 25, 1975, entitled Instrument for the Detection of *Neisseria Gonorrhoeae* and the Like, Ser. No. 561,707, granted May 4, 1976 now U.S. Pat. No. 3,954,564.

Frederick C. Mennen, application filed May 16, 1977, entitled Paper Brooklet for Presumptive Diagnosis of *Neisseria Gonorrhoeae* in the Male, Ser. No. 797,467, granted Aug. 22, 1978, now U.S. Pat. No. 4,108,729.

Application No. 2 in the swab series of Frederick C. Mennen entitled Over the Counter Swab Kit for Self Detection of Gonorrhea in the Male Using Tetramethyl Chromogen Ampul, filed on even date herewith and directed to the preferred use of the hydrochloride salt of the tetramethyl chromogen in the ampule.

BACKGROUND OF THE INVENTION a. Field of the Invention

This invention is in the field of chemistry testing, specifically analytical and analytic control employing test papers and reagent carrier wherein the device is employed in a new manner to obtain an unexpected increase in sensitivity for the direct testing of *Neisseria gonorrhea*.

The invention also lies in the field of molecular biology and microbiology measuring and testing in general and more specifically in testing under the broad principles involving oxidoreductase enzymes from living organisms and particularly involving viable living organisms in which the oxidoreductase is of the peroxidase type.

The invention also lies in the field of sampling in molecular biology and particularly for sampling where the sampling element is in the form of a swab associated with the testing instruments.

The invention further lies in the field of portable testing kits such as the type of kit shown in Dutch Pat. No. 3,748,098 granted July 24, 1973 in which breakable ampuls occupy a compartment and wherein upon breakage of the ampul a solvent flows into the compartment before extraction of a testing reagent which is used in the detection of live viable bacteria.

b. Description of the Prior Art

The closest prior art on the system of testing for Neisseria Gonorrhea in the male is that shown in my recently issued application and granted patents which are listed as follows:

Frederick C. Mennen U.S. Pat. No. 3,876,503;
Frederick C. Mennen U.S. Pat. No. 4,018,653;
Frederick C. Mennen U.S. Pat. No. 3,954,563;
Frederick C. Mennen U.S. Pat. No. 3,954,564;

PATHOTEC PAPERS from Warner-Chilcott as described in Pedersen and Kelley, Public Health Report Vol. 81, No. 4, p. 318 (4/76), Kwalik JAMA Vol. 213 No. 4, p. 626 (7/70), British Journal of Venereal Disease, Vol. 43, p. 73, and Acta Universitatis Carolinae Medica, Vol. 27, No. 129, p. 47-50.

Schulz U.S. Pat. No. 1,221,227 teaches iodine swab for the purpose of applying antiseptic to a cut or bruised area of the body.

Brown et al. U.S. Pat. No. 3,835,834 shows capillary action of a swab placed in a space 20 to draw up liquid contents.

None of the patents in the prior art of swabs show a diagnostic instrument for the detection of the gonorrhea.

A patent to Avery, et al. U.S. Pat. No. 3,450,129, shows a system for transferring inocullum involving the use of a plastic handle fitted with a sterile swab on the end for obtaining a specimen. Swabs on a stick of this type are widely used in taking throat cultures from children and adults who suffer from respiratory infections (Q-tip type, a registered trademark).

The present invention in contrast to the Q-tip applicator sampling device conceives the utilization of a swab of the iodine swab type not for the purpose of applicator of antiseptic to an injured area but rather as a sampling means for immobilizing a specimen of living bacteria for testing gonorrhea.

Patents to Brown, et al. U.S. Pat. No. 3,835,834 and Bucalo U.S. Pat. No. 3,932,223 show the use of capillary action in containing liquid used in the culture of microorganisms or to confine liquid drawn by capillary action into a desired space.

SUMMARY OF THE INVENTION

The invention relates to method and apparatus for an over-the-counter swab kit system for self detection of gonorrhea in the male using saline ampul. The kit comprises a cartridge and a cover. The cartridge holds a pledget ampul and swab at the open end. The pledget is in the form of fibrous material which is impregnated with a chromogenic phenylenediamine salt compound which reacts with *Neisseria gonorrhea* to produce a color change to deep purple. The pledget, before the test, is substantially colorless, is in a dry condition and is activated by a saline wetting agent which is placed in contact with the pledget by breaking an ampul.

The preferred chemical compound which is used and incorporated into the pledget is selected from a group consisting of water soluble hydrochloride salts of phenylenediamines. The ampul holds a sufficient amount of saline (about 1 milliliter). The ampul is a frangible ampul which is broken by squeezing the cartridge and serves to wet the pledget and then is drawn by capillary action through the swab on which a sample of exudated specimen is placed.

In the preferred embodiment the swab system for the detection and diagnosis of living gonorrhea bacteria by chromogenic reaction uses a 1% solution of substantially colorless phenylenediamine hydrochloride salt to impregnate the pledget, thereby permitting diagnosis without transport of the NG bacteria from the sampling swab used for collecting the sample comprising of exudate from the penis of the male. The tubular flexible cartridge having a closed end is preferably of thermoplastic material. The frangible ampul of about 1 ml of sterile saline solution is in a dosage volume sufficient to transport the chromogenic salt in solution through the pledget into the swab. Indented holding means is provided on the cartridge adjacent said pledget to hold said pledget in contiguous relation to said swab whereby the exudate sampled on said swab is detected after the breaking of said ampul which dissolves said chromogenic salt by said saline tp permeate said swab and provide a color diagnosis within less than about three minutes.

The method of the invention comprises the steps of assembling the unit dosage ampul filled with about 1 ml of saline in the cartridge, then inserting a first impregnated fibrous wad of sterile cotton and thereafter inserting the swab which is about the same size as the impregnated fibrous wad. The first wad forming the pledget is a colorless mass of fibrous material which has been impregnated with a 1% N, N, N' N'-tetramethyl-p-phenylenediamine dihydrochloride and then dried to a colorless form.

The step of sealing is to immobilize the first wad in relation to the swab and may be done by dipping the exposed swab tip in liquid acetone which passes backwards and provides an adhesive bond between the plastic material of the cartridge and the cotton at the pledget. After evaporating the acetone the cartridge is ready to be capped with the cover. Another method is to utilize a heated tool to indent the cartridge adjacent to the pledget.

BRIEF DESCRIPTION OF THE DRAWINGS

FIG. 1 is a longitudinal view of the diagnostic device of the present invention;

FIG. 2 is an exploded view of the device of FIG. 1 showing the sealing tape and the protective cover removed;

FIG. 3 is an enlarged transverse cross-sectional view, taken on the line 3—3 of FIG. 1;

FIG. 4 is a longitudinal sectional view of the cartridge assembly of FIG. 2;

FIG. 5 is a modification of the cartridge assembly of FIG. 2;

FIG. 6 is a sectional view showing the device in position for receiving the exudate;

FIG. 7 is a sectional view, showing the device inverted prior to breaking the ampul;

FIG. 8 is a perspective view showing the cartridge in use, the frangible ampule having been broken, the reactive material impregnated into the pledget and a darkened area at the end of the wick indicating the presence of *Neisseria gonorrhoeae;*

FIG. 9 is a longitudinal exploded view of the diagnostic device of the present invention with the protective cover being removed therefrom;

FIG. 10 is elevational view of the diagnostic device in position for receiving the exudate;

FIG. 11 is a longitudinal view of the device of FIG. 1 but showing the protective cover being replaced;

FIG. 12 is an elevational view showing the ampul being broken; and

FIG. 13 is a view similar to FIG. 4 but with the diagnostic device inverted to determine the results of the test.

DESCRIPTION OF THE PREFERRED EMBODIMENTS

As shown in FIGS. 1 and 5 the over the counter swab testing kit (1) (FIG. 1) or 30 (FIG. 5) comprises five basic parts 10 a cover 14 (FIG. 1) or 15 (FIG. 5), (2) a cartridge 12 (FIG. 1 or 32 (FIG. 5), (3) a unit dosage of about 1 ml of saline 26 (FIG. 1) or 46 (FIG. 5) in ampul 13 or 24 at the bottom or closed end of the cartridge, (4) an impregnated pledget 22 above the ampul and (5) a swab 20 (FIG. 1) or 40 (FIG. 5) projecting from the open end of the cartridge.

The cover functions to cover and thereby close the cartridge to prevent comtamination, during storage shipment or use, removable before carrying out the self-test and reattached if desired upon inversion after sampling as shown in FIG. 6 where exudate 28 is touched to the swab 20.

The cartridge bottom may be flat as at 15 in FIG. 1 or winged as at 35 in FIG. 5.

The material of the cartridge 13 in FIG. 4 is thermoplastic and solvent responsive whereby the use of common organic solvents can provide an adhesive bond to retain the impregnated pledget 22.

This means of retaining the pledget is preferred.

An alternate method of retaining the pledget may be used, e.g., a heating tool to indent the cartridge 16 as shown in FIG. 5 at indentation 18.

It is not essential that the indentation be used if the pledget is solvent bonded to the interior wall.

METHOD OF MANUFACTURE OF THE SWAB KIT OF FIG. 1 USING CARTRIDGE WITH FLAT BOTTOM

The manufacture of the swab kit 10 comprises the steps of assembling, sealing and capping the cartridge with the cover. Prefilled ampuls 24 filled with the unit dosage of 1 ml of saline which is prepacked by the manufacturer are placed in the cartridge 10. Sterilization of the assembly is by a process of steam sterilization after placing the ampul in a 2½ inch length of a thermo plastic cartridge formed of a preferred solvent responsive material such as cellulose acetate butyrate (CAB) or cellulose acetate propionate (CAP), these cartridges being supplied by the Eastman Kodak Company of Rochester, N.Y., and being in the form of an openended cylinder. The cartridge is ready for packing the pledget and swab. Cellulose acetate propionate is preferred.

ASSEMBLING

On the top of the ampul there is inserted an impregnated fibrous wad of sterile cotton 22 about ½ inch in length and with the same diameter as the cartridge, e.g., about ⅜ inch high constitutes the pledget. The impregnated wad 22 constituting the pledget is the first wad inserted into the cartridge tube and is placed above the prefilled ampul containing the sterile saline. The first wad forming the pledget is a colorless mass of fibrous material which has been impregnated with a 1% N, N, N' N'-tetramethyl-p-phenylenediamine dihydrochloride and then dried to a colorless form.

The ampul 24 at the bottom of the cartridge prefilled with 1 ml is about 1¼ inches long and the impregnated wad of cotton fibrous material of the same length forms the protruding swab 20, e.g., a wad ½ inch and of the same width, e.g., ⅜ inch is stuffed into the open end of the tube to protrude about ⅛ inch from the open end and this second wad constitutes the swab of the device.

SEALING BY SOLVENT DIPPING

After assembling the elements under sterile conditions in the manufacturing plant, the next phase is the sealing phase in order to immobilize the pledget and the swab with both in the proper relationship to each other above the ampul. This phase is carried out by dipping the exposed tip of cotton fibrous material protruding from the cartridge in a dish of liquid acetone whereby a sufficient quantity of acetone is imbibed and passes backwards through the swab to the interface between the swab and the pledget. After the cartridge is then inverted to permit evaporation removing the assembly from the liquid acetone, the residual acetone imbibed within the cartridge interior softens the interior wall of the cartridge and forms an adhesive bond adjacent to the fibrous material of both the pledget and the swab thereby sealing these in proper position.

ALTERNATE METHOD OF RETAINING THE PLEDGET

Another method of anchoring the pledget in a fixed position within the cartridge is to utilize a tool encircling the cartridge at elevated temperature to indent the cartridge, e.g., above the softening temperature of the plastic material but well below the liquifying temperature of the plastic. The tool pushes in the wall of the cartridge at the outside and bends the plastic inwardly adjacent to the lower edge of the pledget mass and above the ampul. An indentation of 1 to 2 millimeters is adequate to prevent any unwanted movement of the pledget and make it contiguous with the swab.

Of the two methods of locking the pledget and swab in place within the cartridge, the acetone immersion method is preferred since it can be precisely controlled and the odor of acetone serves for quality control. Acetone can be detected in traces to insure that it has substantially disappeared prior to putting the cover in place over this cartridge. This closing of the assembly for shipment is the last step.

THE PRODUCTION OF AND SUPPLIERS FOR CELLULOSE ESTER AMPULE MATERIAL

The suppliers of cellulose ester ampule material are listed in Volume 3, Encyclopedia of Polymer Science and Technology, Interscience Publishers 1965 at pages 345, 350–351, 364–368, and 404–405. Although Eastman Kodak Company supplies the material under the name Kodacel, the propionate from Celanese Plastics, Newark, N.J. or Flex-O-Glass, Inc., Chicago, Ill. is preferred in embodiments which permit precise manufacturing control. If frequently happens that the propionate must be specially ordered and it is preferred to get the material in the desired form and condition from a manufacturer who produces it as a stock item.

The cartridge bottom may be round as in a test tube or it may be pinched as by crimping or it may be flat.

What is claimed is:

1. A self-contained swab cartridge apparatus for the detection and diagnosis of living gonorrhea bacteria by chromogenic reaction with a substantially colorless phenylenediamine hydrochloride salt impregnated pledget without transport of said bacteria from the sampling swab used for collecting the sample comprising of exudate from the penis of the male, said apparatus comprising:

a tubular flexible cartridge having a closed end and an open end holding a frangible ampul of sterile saline solution in a dosage volume sufficient to transport said chromogenic salt in solution;

an ampul made of frangible material filled with a unit dosage of about 1 milliliter of sterile saline for transporting said chromogenic salt brought into solution;

a pledget of fibrous material in the form of a wad containing said chromogenic salt between said ampul and said swab;

a swab protruding from the open end of said cartridge; and indented holding means on said cartridge adjacent said pledget to hold said pledget in contiguous relation to said swab whereby the exudate sampled on said swab is detected after the breaking of said ampul which dissolves said chromogenic salt contained on said pledget by said saline solution to permeate said swab and provide a color diagnosis within less than 3 minutes for the presence of endogenous cytochrome oxidase constituting the metabolite of *Neisseria gonorrhea*.

2. A swab apparatus as claimed in claim 1 including a cover for said swab which fits over said cartridge and which is retained to keep the swab free from contamination.

3. A swab apparatus as claimed in claim 2 wherein said pledget is formed of cotton and is impregnated with 1% N, N, N' N'-tetramethyl-p-phenylenediamine dihydrochloride.

4. A swab apparatus as claimed in claim 3 wherein said hydrochloride is dissolved in water to form a 1% solution and impregnates said pledget to form a substantially color-free wad after drying.

5. A swab apparatus as claimed in claim 4 wherein said cartridge is formed of a transparent thermoplastic material and said indented holding means is a groove formed by heating said cartridge immediately below said pledget to thereby retain said pledget in contiguous relation to said swab.

* * * * *